United States Patent [19]

Waite

[11] Patent Number: 4,485,102

[45] Date of Patent: Nov. 27, 1984

[54] HIGH POTENCY, MYCELIAL-FREE AVOPARCIN ALKYL SULFATE COMPLEX, AND METHOD FOR THE PREPARATION THEREOF

[75] Inventor: Jack P. Waite, Fareham, England

[73] Assignee: American Cyanamid Company, Stamford, Conn.

[21] Appl. No.: 408,369

[22] Filed: Aug. 16, 1982

[51] Int. Cl.³ .............................................. A61K 31/71
[52] U.S. Cl. .................................... 424/181; 424/123
[58] Field of Search ........................ 424/118, 123, 181

[56] References Cited

U.S. PATENT DOCUMENTS

| | | | |
|---|---|---|---|
| 2,786,831 | 3/1957 | Bartels et al. | 424/123 |
| 3,338,786 | 8/1967 | Kunstmann et al. | 424/118 |
| 3,832,462 | 8/1974 | Shu et al. | 424/118 |
| 3,856,937 | 12/1974 | Waite | 424/123 |
| 4,007,167 | 2/1977 | Martin et al. | 424/181 |
| 4,235,878 | 11/1980 | Hiller | 424/94 |
| 4,259,320 | 3/1981 | De Lay | 424/118 |

Primary Examiner—Leonard Schenkman
Assistant Examiner—J. Lipovsky
Attorney, Agent, or Firm—H. G. Jackson

[57] ABSTRACT

The invention is a high potency mycelial-free avoparcin alkyl sulfate complex essentially free of dark colored organic derivatives formed in the fermentative biosynthesis of said antibiotic and a process for the preparation thereof.

3 Claims, 5 Drawing Figures

α-avoparcin   R' = R = Hydrogen
β-avoparcin   R' = Hydrogen, R = Chlorine

α-avoparcin   R' = R = Hydrogen
β-avoparcin   R' = Hydrogen, R = Chlorine

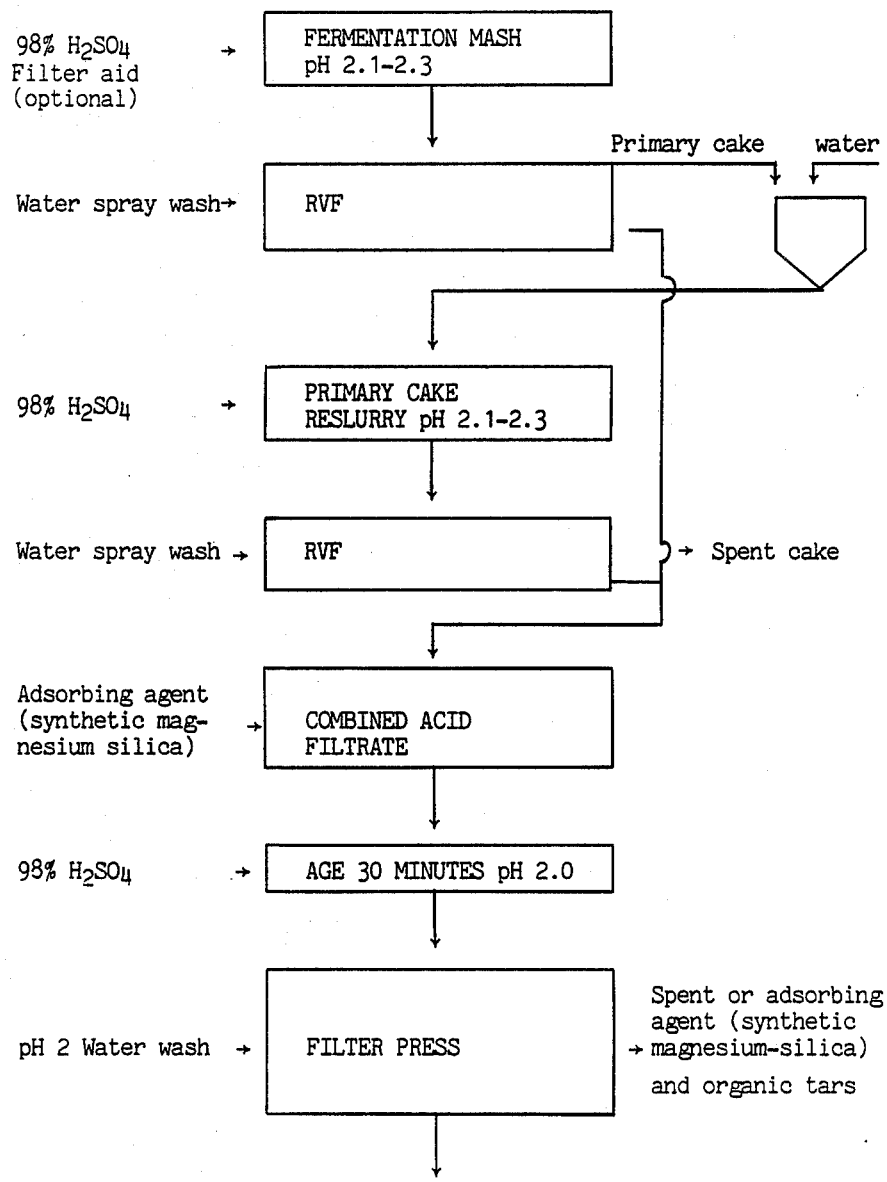

HIGH POTENCY, MYCELIAL-FREE AVOPARCIN ALKYL SULFATE COMPLEX, AND METHOD FOR THE PREPARATION THEREOF

Avoparcin is an important, commercially available, antibiotic used in the feed of meat producing animals to accelerate the growth rate thereof. This antibiotic is generally prepared by a fermentation process and consists essentially of two water-soluble glycopeptides, hereinafter referred to as the $\alpha$ and $\beta$ components of avoparcin. These components are discussed in the following publications: W. J. McGahren, et al *Structure of Avoparcin Components*, Journal of the American Chemical Society, 102, 1671 (1980) and *Avoparcin*, Journal of the American Chemical Society, 101, 2237 (1979).

Figure 1:
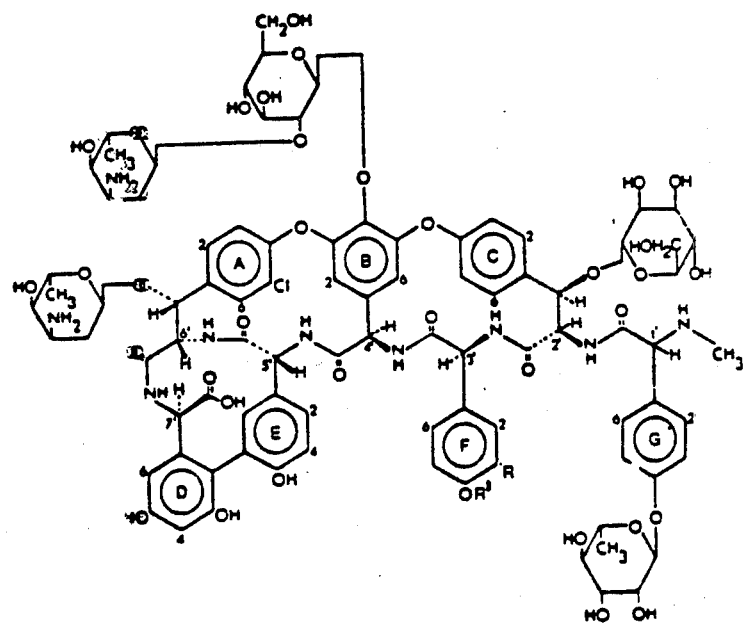

The structure of avoparcin (AV290) is illustrated in FIG. 1. The $\alpha$ component has the configuration shown in FIG. 1, wherein R' and R are each hydrogen and the $\beta$ component is similar excepting that R' is hydrogen and R is chlorine.

When employed as an animal feed additive, avoparcin (the FIG. 1 antibiotic), has generally been administered to said animals, in or with their feed, in the form of an alkyl sulfate complex associated with the dried solids of the whole harvest mash in which it was produced. In practice, this product has been obtained by a process involving, (1) acidification of the antibiotic containing whole harvest mash from the fermentation process; (2) treatment of the acidified whole harvest mash with filter aid and alkali metal alkyl sulfate; (3) filtration of the thus treated acidified mash and (4) drying of the recovered solids which comprise: avoparcin alkyl sulfate complex, filter aid, mycelia and other fermentation insolubles. Although the thus prepared product has been utilized effectively for acceleration of the growth rate of animals for nearly a decade without report of any undesirable side effects or toxicity problems, the relatively low potency of this mycelia containing product limits, to some extent, the marketability of the antibiotic and the physical forms in which it may be administered. As such, a rather extensive research program has been initiated to develop a practical and commercially viable process for the production of high potency mycelial-free avoparcin.

Although the art suggests that avoparcin alkyl sulfate complexes can be obtained in a finished form free of mycelia, unfortunately, the art processes when scaled up to provide the volume of avoparcin alkyl sulfate complex needed by the meat-producing industry are not entirely satisfactory. They are limited by extended filtration periods and consumption of considerable amounts of energy and/or fuel necessary to achieve the degree of drying necessary to provide a dry stable product. Additionally, the physical form and appearance of the avoparcin alkyl sulfate complex produced by the scaled up art process leaves something to be desired.

Surprisingly, it has now been discovered that during the fermentation process in which the antibiotic avoparcin is formed, there are also produced dark colored organic derivatives that appear to be the primary source of the above-mentioned problems. They inhibit filtration, cause tar-like agglomerates to form in the avoparcin alkyl sulfate precipitate and impede the drying of the recoverable product.

While the above-discussion refers to the antibiotic avoparcin, other antibiotics which can be prepared as alkyl sulfate complexes are the basic antibiotics such as BM 123, BM 123 gamma, gentamycin and the aminoglycocides including: streptomycin and neomycin. These antibiotics can be prepared by disclosed fermentative biosynthetic techniques and converted to their respective alkyl sulfate complexes by the process essentially as described above for the preparation of avoparcin alkyl sulfate complexes. The problems encountered in the preparation and use of said antibiotic alkyl sulfate complexes are, however, essentially identical to those encountered in the manufacture and use of the alkyl sulfate complexes of avoparcin. Likewise, improvements in the process for the preparation of alkyl sulfate complexes of the above-identified antibiotics are applicable thereto.

It is, therefore, an object of this invention to provide a high potency, mycelial-free, antibiotic alkyl sulfate complex essentially free of the dark colored organic derivatives produced during antibiotic fermentation and a practical and commercially viable process for the preparation thereof.

It is also an object of this invention to provide a process for the preparation of a high potency, mycelia-free, avoparcin alkyl sulfate complex free of dark colored organic derivatives produced during antibiotic fermentation; and further, to provide a process which will achieve these desired results while markedly reducing the prolonged filtration period normally required to recover the antibiotic complex, eliminating formation of tar-like agglomerates in the precipitated avoparcin alkyl sulfate complex and requiring only minimum consumption of energy and/or fuel for drying the desired product.

In accordance with the process of this invention, the whole harvest fermentation mash containing the antibiotic avoparcin, BM 123, BM 123 gamma, gentamycin, streptomycin or neomycin, is treated with a suitable mineral acid, preferably sulfuric acid, hydrochloric acid or phosphoric acid, to a pH in the range of 1.9 to 2.3. The acidified mash is filtered to separate the antibiotic containing filtrate from the fermentation mash insolubles including the mycelia. Filter aid such as diatomaceous earth may be used to assist filtration, but this is not essential for the process of the invention. The filter cake is generally washed with water to remove trapped antibiotic from the cake and the filtrate therefrom combined with the filtrate from the initial separation. To the mixed acid filtrate is then added about 5 to 50 grams and preferably 7.5 to 40 grams of a highly absorbent, finely divided, inorganic adsorbing agent per liter of acid filtrate. Adsorbing agents which are useful for selectively adsorbing the dark colored organic derivatives from the antibiotic-containing mash acid filtrate, with little or no depletion of the antibiotic in said filtrate, are: magnesium-silica compositions in which the $SiO_2$ to MgO ratio is between 2.2:1 and 6.5:1 and activated carbon. For the most effecient utilization of the adsorbing agent, I have found that the average particle size of the selected adsorbing agent should be between about 2.0 and 15 microns. Among the magnesium-silica compositions which may be employed in the process of the present invention are: attapulgite, magnesium trisilicate and a synthetic hydrated magnesium-silica composition, marketed as Celkate T-21 by Johns Manville.

After thorough mixing of the mash acid filtrate with the selected adsorbing agent, the mixture is filtered, the separated solids washed with water which has been adjusted to a pH between 1 and 3 with strong mineral acid, preferably sulfuric acid or hydrochloric acid, and the filtrates therefrom retained for further treatment. The washed solids may be disposed of or they may be treated with aqueous ammonia, washed with water and recovered for recycling.

The filtrate from the above processing step, which is essentially free of the dark colored organic derivatives and adsorbing agent, is then treated with an aqueous solution containing about 10% to 20% of a commercial grade alkali metal alkyl sulfate. The amount of alkali metal alkyl sulfate added to the suspension is in the range of 0.50 to 1.5 grams and preferably 0.7 to 0.9 grams of alkali metal alkyl sulfate per gram of antibiotic. The suspension is concentrated by any convenient means, as by filtration or settling and decantation, to separate the precipitated solids containing the antibiotic alkyl sulfate complex from the spent liquor. The precipitate is then treated with aqueous ammonia to adjust the pH thereof to between 7.0 and 9.0 and preferably about pH 8.0, and thereafter dried to yield a dry, stable antibiotic alkyl sulfate complex intermediate which is essentially free of mycelia and the dark colored organic derivatives formed during antibiotic fermentation and has an antibiotic potency between 34 and 45%. This dry stable product can be admixed with edible carriers to provide a finished animal feed supplement.

Among the suitable carriers which can be used to prepare the finished animal feed supplements are: soybean meal, alfalfa meal, cornmeal, urea, molasses and the like.

Figure 2:
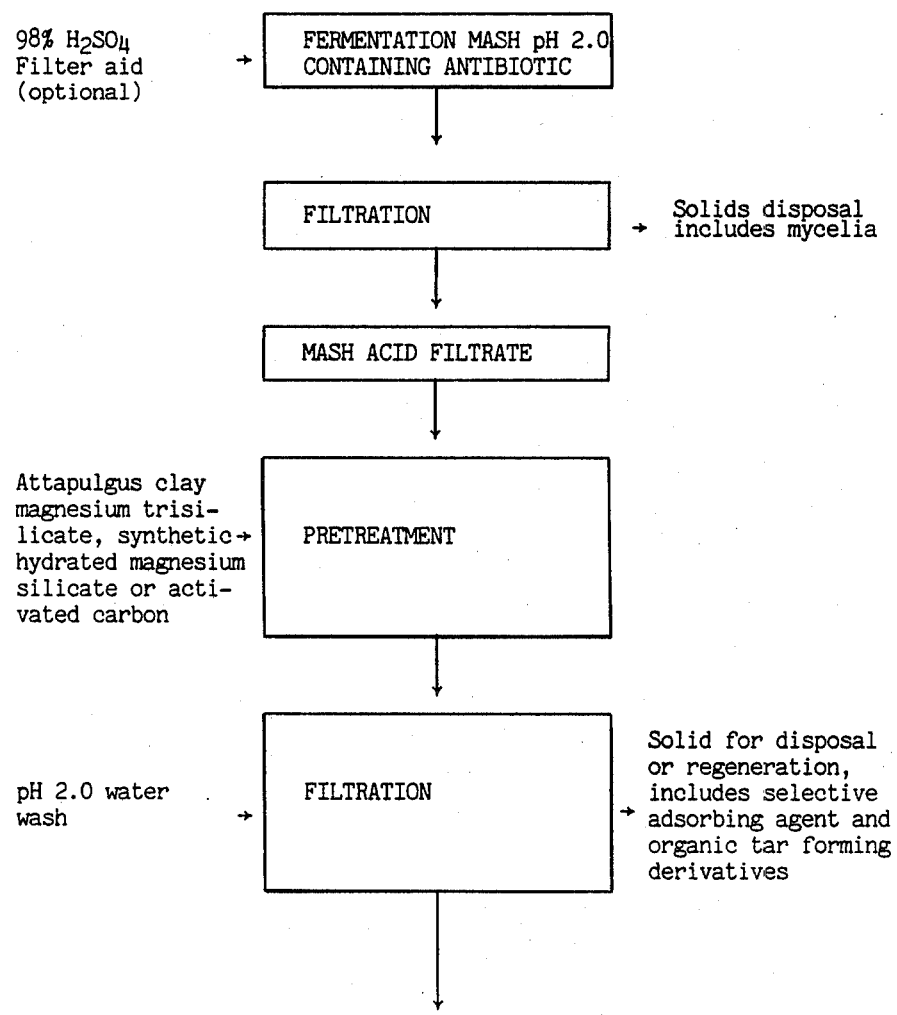
Figure 2A:
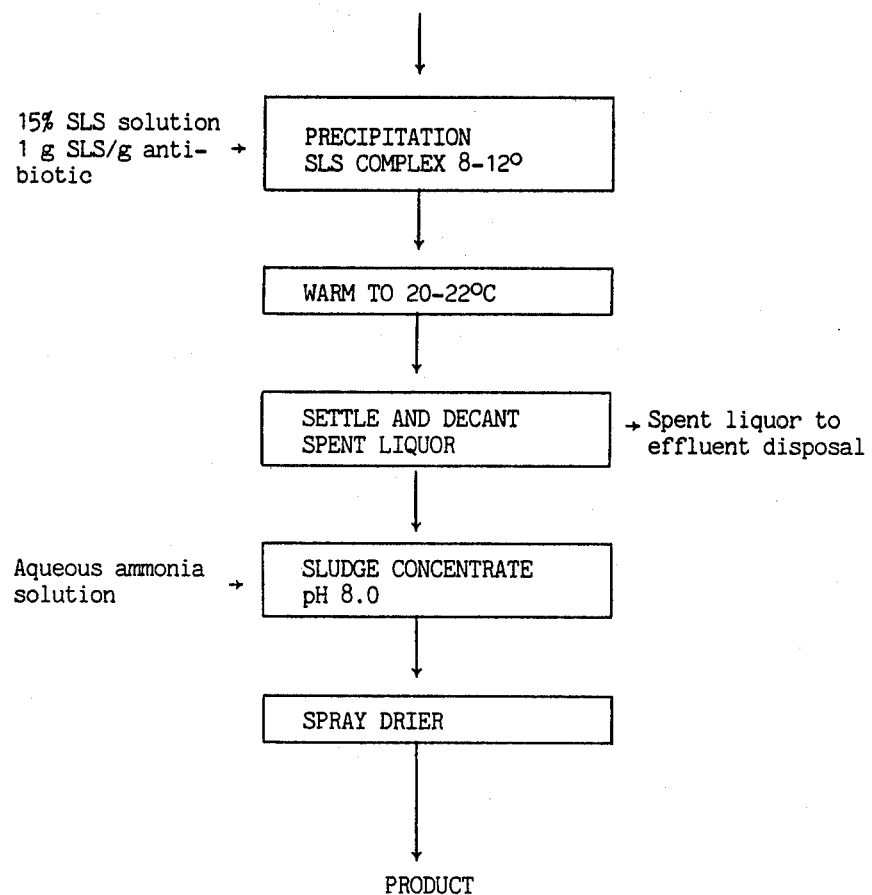

The above process is graphically illustrated in FIGS. 2 and 2a.

The process of this invention is particularly effective for the preparation of avoparcin alkyl sulfate complex. It involves acidification of a whole harvest fermentation mash containing the antibiotic shown in FIG. 1:

The whole harvest fermentation mash is treated with a suitable mineral acid, preferably sulfuric acid, to a pH in the range of 1.9 to 2.3 and preferably 2.1 to 2.3. Other suitable mineral acids include: phosphoric acid and hydrochloric acid. The acidified mash is then filtered by any suitable means as, for example, by a rotary vacuum filter. A small amount of a conventional filter aid may be added to the acidified mash to assist in filtration, but is neither essential nor especially desirable in the preferred process of this invention as herein described. The filtrate from this treatment contains the major portion of the antibiotic from the mash acid filtrate and is routed to a holding vessel for further processing and recovery.

The solids from this filtration are identified as the primary cake. They contain virtually all of the fermentation mash insolubles and minor amount of entrapped antibiotic. To recover the residual entrapped antibiotic the primary cake is slurried with water and treated with mineral acid, preferably sulfuric acid, to adjust the pH of the slurry to between 2.1 and 2.3. The slurry is then filtered by any suitable means such as by a rotary vacuum filter. The filtrate from this treatment is combined with the acid filtrate from the initial filtration and the solids therefrom, containing the mycelia formed in the antibiotic fermentation, disposed of as spent cake.

To the combined acid filtrate, containing the antibiotic and soluble dark colored organic derivatives formed during the antibiotic fermentation, is added a highly selective adsorbent inorganic solid such as attapulgite, magnesium trisilicate, or a synthetic hydrated magnesium-silica composition marketed as Celkate T-21 by Johns Manville. These adsorbents have a $SiO_2$:$MgO$ ratio between 2.2:1 and 6.5:1 and an average particle size in the range of 2 to 15 microns and preferably about 2.9 to 10 microns.

Alternatively, a suitable grade of activated about carbon may be used as the adsorbing agent. However, preferred adsorbents are: attapulgus clay, magnesium trisilicate and a synthetic hydrated magnesium silica composition. The amount added is generally in the range of 5 to 50 grams and preferably 7.5 to 40 grams of adsorbent per liter of mash acid filtrate.

The acid filtrate-adsorbing agent mixture is stirred for about 15 to 45 minutes and preferably about 30 minutes, to permit selective adsorption of the dark colored organic derivatives (i.e. the dark organic color bodies that cause tar-like agglomerates to form in the avoparcin alkyl sulfate precipitate) by the adsorbing agent. If necessary, mineral acid, preferably sulfuric acid is added to the treated acid filtrate mixture to maintain the pH thereof between about 1.9 and 2.3, and preferably about pH 2.0.

After aging, the mixture is filtered, washed with acidified water (pH 2.0) and the solids containing the spent adsorbing agent and organic tar-like components discharged from the system. In practice, the spent solids may be disposed of as waste or they may be treated with aqueous ammonia to dissolve the dark colored organic derivatives and recover the adsorbing agent for recycling.

The acid filtrate, free of mycelia and dark colored organic derivatives, is then cooled to a temperature between about 5° and 15° C. and preferably to 10° to 12° C. An aqueous solution containing about 10 to 20% and preferably 14 to 15% by weight of a commercial grade alkali metal alkyl sulfate is slowly added to the filtrate and the thus formed mixture permitted to age with stirring for about 0.5 to 1.5 hours. During the aging process the temperature of the alkali metal alkyl sulfate-acid filtrate mixture is permitted to warm to about 20° C. Thereafter, the solids are permitted to settle in the mixture and the effluent then removed by decantation or other conventional means.

The amount of alkali metal alkyl sulfate added to the antibiotic containing acid filtrate is in the range of 0.50 to 1.5 grams and preferably 0.75 to 1.0 grams of alkali metal alkyl sulfate per gram of the FIG. 1 avoparcin antibiotic activity measured in the mash acid filtrate.

The alkali metal alkyl sulfates operable in the process of the invention may be represented by the following general formula:

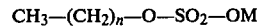

$$CH_3-(CH_2)_n-O-SO_2-OM$$

wherein n is an integer from 9 to 17, inclusive, and M is sodium or potassium. Typical such alkali metal alkyl sulfates which may be employed are, for example, sodium decyl sulfate, potassium hendecyl sulfate, sodium lauryl sulfate, potassium tridecyl sulfate, sodium myristyl sulfate, potassium pentadecyl sulfate, sodium cetyl sulfate, potassium heptadecyl sulfate, and sodium octadecyl sulfate. Mixtures of alkali metal alkyl sulfates may also be employed such as a mixture of sodium hendecyl sulfate and potassium octadecyl sulfate; a mixture of potassium decyl sulfate and sodium heptadecyl sulfate; a mixture of potassium lauryl sulfate and potassium cetyl sulfate; a mixture of sodium tridecyl sulfate, potassium myristyl sulfate, and sodium pentadecyl sulfate; and the like. When mixtures of alkali metal alkyl sulfates are employed, then a corresponding mixture of antibiotic-alkyl sulfate complexes are obtained.

The settled sludge from the above-treatment, containing the antibiotic alkyl sulfate complex, is then neutralized with aqueous ammonia and the neutralized sludge dried by any convenient means as, for example, by spray or freeze drying to give the product. The product has an antibiotic potency between about 31 and 45%, and is approximately 300 to 400% more potent than biomass containing avoparcin products and about 100 to 200% higher in potency than avoparcin alkyl sulfate complexes obtained from somewhat similar processes, but processes that do not provide for the removal of the dark colored organic derivatives from avoparcin mash acid filtrates prior to treatment with an alkali metal alkyl sulfate.

While the above process have been described primarily as it relates to the preparation of avoparcin alkyl sulfate complexes, said process is likewise applicable to the manufacture of the alkyl sulfate complexes of the basic antibiotics mentioned above.

Figure 3A:
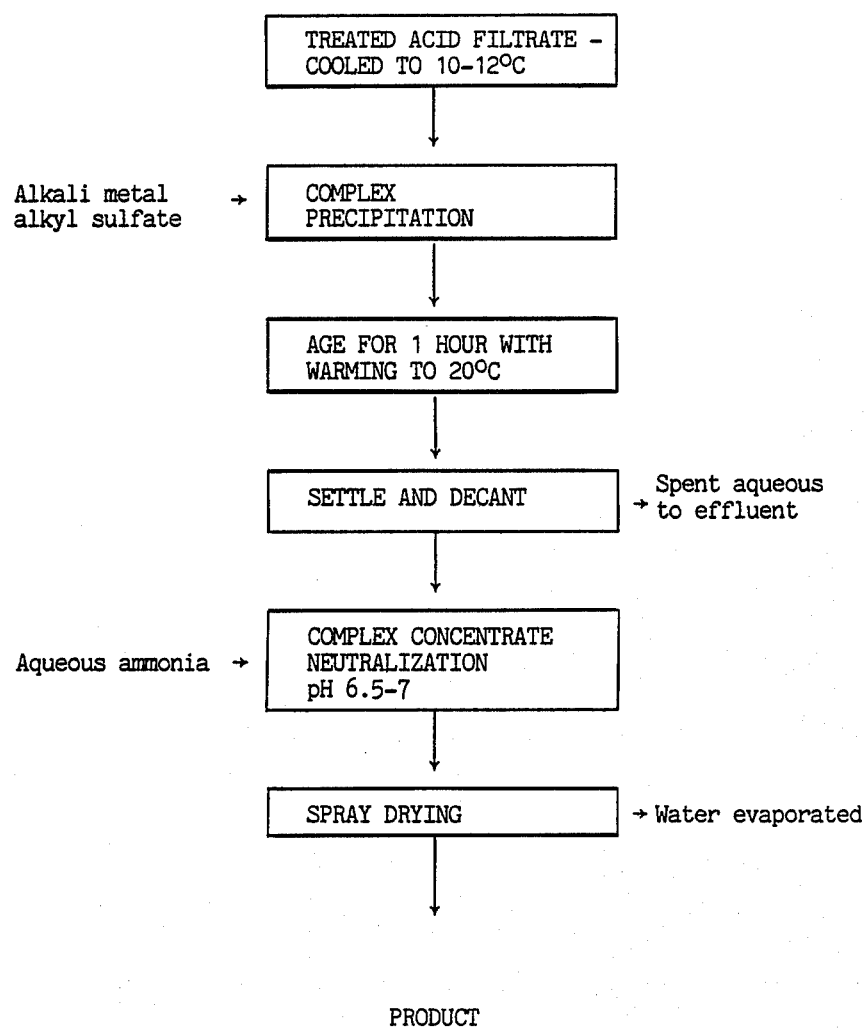

This process is graphically illustrated in FIGS. 3 and 3a.

The present invention is further illustrated by the examples set forth below. These examples are simply illustrative and not intended to limit the scope of the invention.

EXAMPLE I

Precipitation of antibiotic avoparcin sodium lauryl sulfate complex from mash acid filtrate A series of production fermentation mashes, containing the antibiotic avoparcin, were adjusted to pH 2.0–2.3 with 98% sulfuric acid and filtered using a Dicalite precoated Buchner filter. An aqueous 14% solution of sodium lauryl sulfate was slowly added to a 1 liter sample of the acid filtrate. In the early stages of addition a fine, gelatinous precipitate formed which was virtually impossible to separate either by filtration or by centrifuge. Separation could only be achieved by filtration using an excessively high level of filter aid. Also, as precipitation of the avoparcin lauryl sulfate complex approached the 90% level, the particles began to agglomerate and become tar-like in consistency. On further sodium lauryl sulfate addition when precipitation was in excess of about 90%, the particles flocculated and then agglomerated into large, semi-liquid tar-like lumps. No satisfactory method for separating the lauryl sulfate complex from these tarry lumps was found.

EXAMPLE II

Precipitation of antibiotic avoparcin lauryl sulfate complex from mash acid filtrate in the presence of calcium carbonate The procedure of Example 1 was repeated excepting that 3 to 5 liter samples of mash acid filtrate were used and 15 to 20 grams $CaCO_3$ was added to the pH 2 mash acid filtrate. Partial solution of the $CaCO_3$ occurred and the pH of the solution increased to 4.1 to 4.3. The pH of the mixtures were readjusted to 2 to 2.1 with sulfuric acid. Complete solution occurred and calcium sulfate began to precipitate fairly slowly on aging. An aqueous 14% solution of sodium lauryl sulfate was added to each sample and co-precipitation of calcium sulfate and avoparcin lauryl sulfate was observed in each sample. Initially, the precipitate was found to be homogeneous in each sample and each showed good filtration characteristics. However, it was found that all slurries, when aged for 30 minutes, began to segregate. The antibiotic complex in each sample agglomerated and separated into bar-like lumps from which the complex could not be readily recovered.

EXAMPLE III

Precipitation of antibiotic avoparcin lauryl sulfate complex from mash acid filtrate in the presence of calcium hydroxide The procedure of Example 1 was again repeated excepting that 3 to 5 liter samples of mash acid filtrate were used and $Ca(OH)_2$ was added to the pH 2 mash acid filtrate. The mash acid filtrate samples were treated with a 20% aqueous lime slurry and adjusted to pH 7 to 9 therewith. A 14% sodium lauryl sulfate solution was then added and the pH adjusted very slowly to 2.0 by addition of 98% sulfuric acid. A precipitate containing the avoparcin lauryl sulfate complex forms and is homogeneous and easily filtered at first. However, as in the previous example, segregation of the complex in the form of a tar occurs when the mixture is permitted to stand for a short time, i.e., about 30 minutes. The product was recovered and assayed for antibiotic potency. It was found that said product has a potency in the range of 17 to 22%. Data obtained are reported below.

| Experiment no | 1 | 2 | 3 | 4 | Mean |
|---|---|---|---|---|---|
| Assay, mash acid filtrate g/l | 13.64 | 12.00 | 10.45 | 10.45 | 11.64 |
| g SLS/g avoparcin in treated acid filtrate | 0.69 | 0.82 | 1.0 | 1.0 | 0.88 |
| % Efficiency | | | | | |
| Treated filtrate/spray dried product | 98.8 | 96.9 | 102.9 | 93.8 | 98.1 |
| Overall | 90.0 | 91.1 | 98.0 | 87.6 | 91.8 |
| Assay spray dried product % 'd.b.' | 21.68 | 20.6 | 18.7 | 17.45 | 19.6 |

When these data are compared with the data obtained by the process of the present invention, i.e. Examples 7–9, it can be seen that the process of the invention provides a 100 to 200% improvement in the potency of the recovered avoparcin lauryl sulfate complex, over that obtained by the above treatment.

EXAMPLE IV

Precipitation of antibiotic avoparcin lauryl sulfate complex from mash acid filtrate in the presence of a variety of finely divided solid adsorbing agents In these tests whole harvest fermentation mash containing the antibiotic avoparcin, the mycelia and all of the components developed in the fermentation procedure, was filtered. The acid filtrate was then divided into samples of equal volume and the separate samples treated with 50 g/l of firmly divided attapulgite, bentonite, montmorillonite, powdered cellulose, magnesium trisilicate or a synthetic hydrated magnesium-silica composition and a sufficient amount of an aqueous solution containing 14% by weight of sodium lauryl sulfate, to provide 1.0 gram of sodium lauryl sulfate per gram of avoparcin antibiotic measured in the mash acid filtrate. The mixtures were stirred for 30 minutes, allowing the avoparcin lauryl sulfate to form, and then permitted to settle. In each instance it was observed that dark brown tar-like agglomerates formed in each of the precipitated solids. As such, all treatments were unsatisfactory.

EXAMPLE V

Preparation of antibiotic avoparcin lauryl sulfate complex from mash acid filtrate pretreated with a variety of finely divided solid adsorbing agents In these tests, acidified whole harvest fermentation mash containing the avoparcin antibiotic, the mycelia and all of the components developed in the fermentation procedure was filtered. The acid filtrate was then divided into samples of equal volume and the separate samples treated with 50 g/l of finely divided attapulgite, bentonite, montmorillonite, powdered cellulose, magnesium trisilicate or synthetic magnesium silica composition. Each of the mixtures was stirred for 30 minutes and then filtered. The solids from each mixture was recovered and examined for color.

In this evaluation adsorbing agents that adsorb significant amounts of the tar-forming components from the mash acid filtrate become dark brown in color. Also, when these agents are washed with aqueous ammonia the adsorbed tar-forming components are dissolved by the wash solution giving it a dark brown color and returning the solid adsorbing agent to its natural appearance.

In these tests it was observed that there was a very significant reduction in the color of the mash acid filtrates treated with attapulgite, magnesium trisilicate and synthetic hydrated magnesium-silica composition. However, there was *no* significant alteration in the color of the mash acid filtrated that had been treated with bentonite, montmorillonite or powdered cellulose.

Furthermore, the recovered attapulgite, magnesium trisilicate and synthetic hydrated magnesium-silica compositions, from the above treatments were dark brown; whereas, the recovered bentonite, montmorillonite and powdered cellulose, from said treatments were virtually unchanged from their natural color. Thus, it was surprisingly found that attapulgite, magnesium trisilicate and synthetic hydrated magnesium-silica compositions, are highly selective as adsorbing agents for the tar-forming constituents found in the acidified whole harvest antibiotic fermentation mash.

Portions of each of the above-treated mash acid filtrates were then treated with an aqueous solution containing 14% by weight of sodium lauryl sulfate. Enough sodium lauryl sulfate solution was added to each sample to provide 1.0 grams of avoparcin antibiotic measured in the mash acid filtrate.

The precipitated solids in each of the mash acid filtrates pretreated with attapulgite, magnesium trisilicate or synthetic hydrated magnesium-silica composition, were cream colored and there was *no* evidence of agglomeration or tar-formation in the precipitated avoparcin lauryl sulfate complexes. However, mash acid filtrates that were pretreated with bentonite, powdered cellulose or montmorrilonite yielded chocolate brown precipitates containing the tar-like agglomerates.

From the above data, it can be seen that attapulgite, magnesium trisilicate and synthetic hydrated magnesium-silica composition, are unexpectedly effective selective adsorbing agents for organic tar-forming components of acidified antibiotic whole harvest fermentation mash; and that bentonite, montmorillonite and powdered cellulose are *not* selective for this purpose.

From the data represented below, it can also be seen that the $SiO_2:MgO$ ratio of the selective adsorbing agents is between 2.2:1 to 6.5:1; whereas, the nonselective noneffective, adsorbing agents have an $SiO_2:MgO$ ratio of 16.4:1 or higher.

| % Composition as | Chemical composition of selective and non-selective adsorbing agents | | | | |
|---|---|---|---|---|---|
| | Synthetic hydrated magnesium-silica composition | Attapulgite | Magnesium trisilicate | Bentonite | Montmorillonite |
| $SiO_2$ | 65.5 | 68.0 | 68.5 | 64.17 | 68.96 |
| MgO | 14.9 | 10.5 | 31.5 | 3.90 | 1.53 |
| $Al_2O_3$ | 4.0 | 12.0 | — | 17.14 | 11.67 |
| CaO | 0.4 | 1.7 | — | 1.48 | 1.47 |
| $Fe_2O_3$ | 1.1 | 5.0 | — | 4.81 | 6.28 |
| Others | 14.1 | 2.8 | — | — | — |
| Ratio | | | | | |
| $SiO_2:MgO$ | 4.4:1 | 6.5:1 | 2.2:1 | 16.4:1 | 45.0:1 |

Significant physical properties of attapulgite and synthetic hydrated magnesium-silica composition useful as selective adsorbing agents for tar-forming components of antibiotic mash acid filtrate:

| Physical property | Synthetic hydrated magnesium-silica composition | Attapulgite |
|---|---|---|
| Average particle size, microns | 10 | 2.9 (95% finer than 10) |
| Specific gravity | 2.41 | 2.45 |
| Surface area, $m^2/g_3$ | 180.0 | 125.0 |
| Bulk density, lbs/ft | 12.8 | 14.0 |

EXAMPLE VI

Determination of effectiveness of adsorbents for selectively removing organic tar-forming constituents from antibiotic mash acid filtrate with little or no depletion of the antibiotic content thereof Following the procedure described in connection with FIGS. 2 and 2a, aliquots of avoparcin mash acid filtrate (pH 2.0) were treated by stirring with various amounts of each adsorbent being evaluated. The treated filtrates were stirred for 30 minutes and then filtered to remove the adsorbent and determine whether the adsorbents would selectively remove organic tar-forming constituents from the avoparcin mash acid filtrate.

The colors of the resulting filtrates from the above-procedure were measured by optical comparator against Hazen color standards and the avoparcin content of the filtrates determined by high pressure liquid chromotography (HPLC).

Results obtained are reported below.

| Adsorbent | Treatment level (g/l) | Color of filtrate Hazen Units (diluted 2:1 with water) | Avoparcin HPLC assay of filtrate (g/l) |
|---|---|---|---|
| Untreated acid filtrate | — | 500 | 10.20 |
| Attapulgite Powder | 10.0 | 350 | 9.76 |
| | 20.0 | 300 | 9.56 |
| | 30.0 | 200 | 9.22 |
| | 40.0 | 150/200 | 9.13 |
| Attapulgite Granules 30/60 | 10.0 | 400 | 9.89 |
| | 20.0 | 350 | 9.59 |
| | 30.0 | 300 | 9.50 |
| | 40.0 | 200 | 9.35 |
| Synthetic hydrated magnesium-silicia composition | 10.0 | 450 | 10.17 |
| | 20.0 | 400 | 10.24 |
| | 30.0 | 350 | 10.22 |
| | 40.0 | 300 | 10.27 |
| Activated carbon | 2.5 | 400 | 10.18 |
| | 5.0 | 350 | 10.09 |
| | 7.5 | 200 | 9.90 |
| | 10.0 | 150/200 | 9.78 |

EXAMPLE VII

Preparation of avoparcin lauryl sulfate complex from mash acid filtrate

Two, 2.5 liter samples of avoparcin mash acid filtrate (pH 2) from which mycelia had been removed by filtration were stirred with synthetic magnesium-silica composition for 15 minutes. The pH of the treated mixtures were readjusted to 2.0 and aging of the mixtures was continued for an additional 15 minutes. The synthetic hydrated magnesium-silica (SHMSC) composition was then filtered off and displacement washed with 500 ml of water adjusted to pH 2.0 with $H_2SO_4$.

The filtrates were combined and treated with a 14% aqueous solution of sodium lauryl sulfate which caused precipitation of the cream colored avoparcin lauryl sulfate. No segregation and no tar-forming agglomerates were noted in the precipitate.

The avoparcin-lauryl sulfate complex was concentrated by decantation and the product obtained by spray drying of the sludge which had been neutralized to a pH between 6.5 and 7.0 with aqueous ammonia. The results of these tests appear below.

| | Experiment no | |
|---|---|---|
| | 1 | 2 |
| SHMSC, g/l | 40.0 | 50.0 |
| Assay, mash acid filtrate, g/l | 16.68 | 16.68 |
| g SLS/g avoparcin in treated acid filtrate | 0.82 | 0.85 |
| % Efficiency | | |
| mash acid filtrate/treated filtrate | 100.0 | 99.6 |
| treated filtrate/spray dried product | 92.35 | 92.3 |
| Overall | 92.35 | 91.9 |
| Assay spray dried product % 'd.b.' | 38.0 | 36.4 |

SLS = Sodium lauryl sulfate
SHMSC = Synthetic hydrated magnesium-silica composition

EXAMPLE VIII

Process for the preparation of mycelia-free and tar-free avoparcin lauryl sulfate complex, complete from fermentation mash to spray dried product A series of preparations were carried out to obtain overall process efficiency data from fermentation mash to the spray dried, mycelial-free, tar-free product. The process employed in this evaluation is illustrated in FIGS. 3 and 3a.

In all cases, mash extraction was carried out at pH 2.0 (98% sulfuric acid) with a secondary extraction of the primary spent cake using 600 ml water per kg starting mash. The resulting combined acid filtrate (CAF) was treated with synthetic hydrated magnesium-silica composition (SHMSC) at pH 2.0, filtered and the filter residue displacement washed with water at pH 2.0 ($H_2SO_4$).

The avoparcin-lauryl sulfate complex was precipitated from the treated acid filtrate (TAF) using the same procedure as described in connection with FIGS. 3 and 3a. The complex slurry was concentrated by settling and decantation, the concentrate neutralized (pH 6.5–7) with aqueous ammonia and then spray dried to yield the product.

The results for a series of 3 preparations are summarized below.

| | Fermentation mash batch no | | | |
|---|---|---|---|---|
| | 3 | 4 | 5 | Mean |
| Quantity mash extracted, kg | 1 | 1 | 1 | — |
| Assay of mash, g/kg | 14.08 | 17.34 | 14.77 | — |
| % Efficiency: | | | | |
| mash/CAF | 90.0 | 92.8 | 91.0 | 91.2 |
| CAF/TAF | 96.5 | 100.0 | 98.0 | 98.2 |
| TAF/spray dried product | 96.3 | 94.4 | 95.9 | 95.5 |
| Overall mash/ spray dried F.I. | 83.6 | 87.6 | 85.5 | 85.6 |
| g SLS/g Avoparcin in TAF | 1.19 | 0.91 | 0.94 | 1.01 |
| Assay spray dried product % 'd.b.' | 34.6 | 41.2 | 34.8 | 36.9 |

EXAMPLE IX

Process for the preparation of mycelial-free and tar-free avoparcin lauryl sulfate complex, complete from fermentation mash to spray dried product In this evaluation the process described in connection with FIGS. 3 and 3a was employed.

Avoparcin whole harvest fermentation acidified to pH 2.0 with 98% $H_2SO_4$ and filtered, using a rotary vacuum filter to separate the mycelia from the antibiotic containing filtrate.

A 6 liter portion of the mash acid filtrate (pH 2.0) was then treated with 50 g/l of synthetic hydrated magnesium-silica composition with readjustment of the pH to 2.0.

The spent adsorbent was filtered off and displacement washed with 1 liter of water pH 2.0 ($H_2SO_4$). The total volume of filtrate plus wash recovered was 6.6 liters.

The complex was precipitated by the slow addition of 650 ml of 15% "real" sodium lauryl sulfate at 8°–10° C.

The resulting slurry was slowly warmed to 22° C. with stirring.

After settling for 30 minutes, 5.26 liters of essentially clear supernatant were decanted off.

The remaining sludge concentrate was neutralized with aqueous ammonia and spray dried to recover the product.

| Assay | g/l |
|---|---|
| Initial mash acid filtrate | 12.70 |
| Treated acid filtrate | 11.49 |
| % Efficiency | % |
| Mash acid filtrate/treated filtrate | 99.5 |
| Treated filtrate/decanted liquor | 3.1 |
| Treated filtrate/spray dried product | 97.85 |
| Overall | 97.36 |
| Avoparcin balance | 101.45 |
| g SLS/g Avoparcin in treated filtrate | 1.285 |
| Assay of spray dried product, % 'd.b.' | 30.6 |

In these determinations it was found that synthetic hydrated magnesium-silica composition was highly effective for removing organic tar-forming components from antibiotic mash acid filtrate. It was also found that removal of the organic-tar forming constituents in the filtrate, prior to treatment with an alkali metal alkyl sulfate, eliminated agglomeration of tars in the precipitated antibiotic lauryl sulfate complex and that almost quantitative recovery of the avoparcin could be achieved with the process of this invention.

I claim:

1. A process for the preparation of a high potency, mycelial-free antibiotic avoparcin, BM123, BM123 gamma, gentamycin streptomycin or neomycin alkyl sulfate complex essentially free of dark colored organic derivatives formed during antibiotic fermentation, comprising the steps of:

(a) producing a fermentation liquor or acidifying the whole harvest mash to a pH of from 1.9 to 2.3 with a pharmacologically acceptable acid and filtering the acidified mash to obtain the acid filtrate substantially free of mycelia and fermentation insolubles;

(b) adding to the mycelial-free acid filtrate from 5 to 50 grams per liter of filtrate of a highly absorbent, finely divided, inorganic solid absorbing agent of a magnesium-silica composition in which the $SiO_2$ to MgO ratio is between 2.2:1 and 6.5:1 or activated carbon which is selective for the adsorption of dark colored organic derivatives formed during antibiotic fermentation;

(c) agitating the thus formed mixture for from 15 to 45 minutes and separating the adsorbent solids and dark colored organic derivatives from the antibiotic containing acid filtrate;

(d) adding to the acidified filtrate, from which the adsorbent solids and dark colored organic derivatives have been removed, 0.5 to 1.5 grams of a complexing agent of compounds of the formula: $CH_3-(CH_2)_n-O-SO_2-OM$ wherein n is an integer from 9 to 17, inclusive, and M is sodium or potassium, or mixtures thereof per gram of antibiotic activity measured in the filtrate;

(e) concentrating the solids in the alkali metal alkyl sulfate-treated acidified liquor and separating the spent liquor from the solids which contain the antibiotic alkyl sulfate complex;

(f) treating the antibiotic containing solids with aqueous ammonia to adjust the pH thereof to between 6.5 and 9.0 and thereafter drying the resulting mixture to recover the high potency mycelial-free, antibiotic alkyl sulfate complex, essentially free of dark colored organic derivatives formed during antibiotic fermentation.

2. A process for the preparation of a high potency, mycelial-free avoparcin alkyl sulfate complex according to claim 1, wherein the whole harvest mash is adjusted to a pH between 1.9 and 2.3 with sulfuric acid; the adsorbing agent is a magnesium-silica composition in which the $SiO_2$ to MgO ratio is between 2.1:1 and 6.5:1 or activated carbon and is admixed with the antibiotic containing mycelial-free, acid filtrate in sufficient amount to provide 5 to 50 grams of adsorbing agent per liter of acid filtrate; and the alkali metal alkyl sulfate is admixed with the avoparcin containing mycelial-free acid filtrate, from which the dark colored organic derivatives formed in antibiotic fermentation and the selective adsorbing agent have been removed, the alkali metal alkyl sulfate being added in sufficient amount to provide from 0.5 to 1.5 grams of alkali metal alkyl sulfate per gram of avoparcin activity measured in the filtrate.

3. A process according to claim 2 wherein the adsorbing agent is attapulgite, magnesium trisilicate or a synthetic hydrated magnesium-silica composition having an average particle size of from 2 to 15 microns and the alkali metal alkyl sulfate is sodium lauryl sulfate.

* * * * *